US008753884B2

(12) United States Patent
Cibelli et al.

(10) Patent No.: US 8,753,884 B2
(45) Date of Patent: Jun. 17, 2014

(54) METHOD OF DIFFERENTIATION OF MORULA OR INNER CELL MASS CELLS AND METHOD OF MAKING LINEAGE-DEFECTIVE EMBRYONIC STEM CELLS

(75) Inventors: Jose Cibelli, East Lansing, MI (US); Michael D. West, Mill Valley, CA (US); Robert Lanza, Clinton, MA (US)

(73) Assignee: Advanced Cell Technology, Marlborough, MA (US)

( * ) Notice: Subject to any disclaimer, the term of this patent is extended or adjusted under 35 U.S.C. 154(b) by 0 days.

(21) Appl. No.: 12/152,779

(22) Filed: May 16, 2008

(65) Prior Publication Data

US 2009/0104697 A1    Apr. 23, 2009

Related U.S. Application Data

(63) Continuation of application No. 11/025,893, filed on Dec. 29, 2004, now abandoned, which is a continuation of application No. 10/625,653, filed on Jul. 24, 2003, now abandoned, which is a continuation of application No. 09/689,743, filed on Oct. 13, 2000, now abandoned.

(60) Provisional application No. 60/159,550, filed on Oct. 15, 1999.

(51) Int. Cl.
*C12N 5/00* (2006.01)
*C12N 5/02* (2006.01)
*C12N 15/00* (2006.01)

(52) U.S. Cl.
USPC ........... 435/377; 435/366; 435/378; 435/379; 435/320.1

(58) Field of Classification Search
USPC .................. 435/377, 366, 378, 379, 320.1
See application file for complete search history.

(56) References Cited

U.S. PATENT DOCUMENTS

| | | | | |
|---|---|---|---|---|
| 5,843,780 | A | * | 12/1998 | Thomson ...................... 435/363 |
| 5,942,435 | A | | 8/1999 | Wheeler |
| 5,945,577 | A | | 8/1999 | Stice et al. |
| 6,235,970 | B1 | * | 5/2001 | Stice et al. ...................... 800/24 |
| 2006/0148078 | A1 | * | 7/2006 | Gerecht-Nir et al. ......... 435/366 |

FOREIGN PATENT DOCUMENTS

| | | |
|---|---|---|
| JP | 08-502652 | 5/1994 |
| WO | 9807841 | 2/1998 |
| WO | WO 98/30683 A2 | 7/1998 |
| WO | 9901163 | 1/1999 |
| WO | WO 99/16864 A1 | 4/1999 |
| WO | 9945100 | 9/1999 |
| WO | 0119977 | 3/2001 |

OTHER PUBLICATIONS

Thomson. Science, 282: 1145-1147, 1998.*
Smith et al. J. Tiss. Cult. Meth., 13: 89-94, 1991.*
Chen et al. Stem Cells, 21: 281-295, 2003.*
Duray et al. Science and Med, 4(3): 46-55, 1997.*
Wianny et al. Biology of Reproduction, 57: 756-764, 1997.*
Schuldiner et al. 2000, PNAS, 97:11307.*
Li et al., Blood, 98: 335-342, 2001.*
Bongso et al., Human Reproduction, 9(11): 2110-7, 1994.*
Cibelli et al., "Transgenic bovine chimeric offspring produced from somatic cell-derived stem-like cells", Nature Biotechnology, Nature Puglishing, vol. 16, Jul. 1998 pp. 642-646.
Deng et al., "Fibroblast Growth Factor Receptor-1 (FGFR-1) Is Essential for Normal Neural Tube and Limb Development", Developmental Biology, vol. 185, No. 1, May 1997 pp. 42-54.
Gallicchio et al., "Suppression of Hematopoietic Support Function is Associate with Over-Expression of IL-4 and TGFB1 in LP-BM5 MuIV Infected Stromal Cell Lines", Antiviral Research, vol. 26, No. 3, Mar. 1995, p. A273.
Lanza et al., "Prospects for the use of nuclear transfer in human transplantation", Nature Biotechnology, Nature Publishing, vol. 17, No. 12, Dec. 1999, pp. 1171-1174.
Parrow et al., "Trophoblastic Vesicles Produce Factors Capable of Stimulating Proliferation of Undifferentiated Bovine Blastocyst Derived Cells in Culture", Theriogenology, vol. 47, No. 1, Jan. 1997, p. 243.
Pittenger et al., "Multilineage Potential of Adult Human Mesenchymal Stem Cells", Science, American Associate for the Advancement of Science, vol. 284, Apr. 1999 pp. 143-147.
Stekelenburg-Hamers et al., "Isolation and Characterization of Permanent Cell Lines from Inner Cell Mass Cells of Bovine Blastocysts", Molecular Reproduction and Development, Lisss, NY, vol. 40, No. 4, Apr. 1995 pp. 444-454.
Sturm et al., "Unrestricted lineage differentiation of parthenogenetic ES cells", Development, Genes and Evolution, Berlin, vol. 206, No. 6, (1997) pp. 377-388.
Thompson et al., "Neural differentiation of rhesus embryonic stem cells", APMIS, Copenhagen, DK, vol. 106, (1998), pp. 149-156.
Thompson et al., "Embryonic Stem Cell Lines Derived from Human Blastocysts", Science, American Association for the Advancement of Science, vol. 282, Nov. 1998, pp. 1145-1147.
Thomson; Embryonic stem cell lines derived from human blastocysts (1998) Science 282:1145.
Zwaka; A germ cell origin of embryonic stem cells? (2005) Development 132:227.

* cited by examiner

*Primary Examiner* — Thaian N Ton
(74) *Attorney, Agent, or Firm* — E. Stewart Mittler

(57) ABSTRACT

An improved method of producing differentiated progenitor cells comprising obtaining inner cell mass cells from a blastocyst and inducing differentiation of the inner cell mass cells to produce differentiated progenitor cells. The differentiated progenitor cells may be transfected such that there is an addition, deletion or alteration of a desired gene. The differentiated progenitor cells are useful in cell therapy and as a I source of cells for the production of tissues and organs for transplantation. Also provided is a method of producing a lineage-defective human embryonic stem cell.

15 Claims, No Drawings

METHOD OF DIFFERENTIATION OF MORULA OR INNER CELL MASS CELLS AND METHOD OF MAKING LINEAGE-DEFECTIVE EMBRYONIC STEM CELLS

CROSS REFERENCE TO PRIOR APPLICATIONS

This application is a continuation of U.S. patent application Ser. No. 11/025,893, filed Dec. 29, 2004, which is a continuation of U.S. patent application Ser. No. 10/625,653, filed Jul. 24, 2003, which is a continuation of U.S. patent application Ser. No. 09/689,743, filed Oct. 13, 2000, which claims the benefit of U.S. Provisional Application No. 60/159,550, filed Oct. 15, 1999, all of which applications are incorporated herein by reference.

BACKGROUND OF THE INVENTION

1. Field of the Invention

The present invention relates to a method of differentiation of the cells of a morula or the inner cells of a blastocyst. These cells can be used for cell therapy and for the generation of cells and organs for isogenic, allogeneic and/or xenogeneic transplantation. The present invention also relates to the production of lineage-defective embryonic stem cells which will not differentiate into specific differentiated lineages, such as mesoderm, endoderm or ectoderm.

2. Description of the Related Art

Methods for deriving embryonic stem (ES) cell lines in vitro from early preimplantation mouse embryos are well known. (See, e.g., Evans et al., *Nature*, 29:154-156 (1981); Martin, *Proc. Natl. Acad. Sci., USA*, 78:7634-7638 (1981)). ES cells can be passaged in an undifferentiated state, provided that a feeder layer of fibroblast cells (Evans et al., Id.) or a differentiation inhibiting source (Smith et al., *Dev. Biol.*, 121:1-9 (1987)) is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency (Bradley et al., *Nature*, 309:255-256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like preimplantation livestock embryos support the development of enucleated oocytes to term (Smith et al., *Biol. Reprod.*, 40:1027-1035 (1989); and Keefer et al., *Biol. Reprod.*, 50:935-939 (1994)). This is in contrast to nuclei from mouse embryos which beyond the eight-cell stage after transfer reportedly do not support the development of enucleated oocytes (Cheong et al, *Biol. Reprod.*, 48:958 (1993)). Therefore, ES cells from livestock animals are highly desirable because they may provide a potential source of totipotent donor nuclei, genetically manipulated or otherwise, for nuclear transfer procedures.

Some research groups have reported the isolation of purportedly pluripotent embryonic cell lines. For example, Notarianni et al., *J. Reprod. Fert. Suppl.*, 43:255-260 (1991), reports the establishment of purportedly stable, pluripotent cell lines from pig and sheep blastocysts which exhibit some morphological and growth characteristics similar to that of cells in primary cultures of inner cell masses isolated immunosurgically from sheep blastocysts. Also, Notarianni et al., *J. Reprod. Fert. Suppl.*, 41:51-56 (1990) discloses maintenance and differentiation in culture of putative pluripotential embryonic cell lines from pig blastocysts. Gerfen et al., *Anim. Biotech*, 6(1):1-14 (1995), discloses the isolation of embryonic cell lines from porcine blastocysts. These cells are stably maintained in mouse embryonic fibroblast feeder layers without the use of conditioned medium, and reportedly differentiate into several different cell types during culture.

Further, Saito et al., *Roux's Arch. Dev. Biol.*, 201:134-141 (1992) reports cultured, bovine embryonic stem cell-like cell lines which survived three passages, but were lost after the fourth passage. Handyside et al., *Roux's Arch. Dev. Biol.*, 196:185-190 (1987) discloses culturing of immunosurgically isolated inner cell masses of sheep embryos under conditions which allow for the isolation of mouse ES cell lines derived from mouse inner cell masses. Handyside et al. reports that under such conditions, the sheep inner cell masses attach, spread, and develop areas of both ES cell-like and endoderm-like cells, but that after prolonged culture only endoderm-like cells are evident.

Recently, Cherny et al., *Theriogenology*, 41:175 (1994) reported purportedly pluripotent bovine primordial germ cell-derived cell lines maintained in long-term culture. These cells, after approximately seven days in culture, produced ES-like colonies which stained positive for alkaline phosphatase (AP), exhibited the ability to form embryoid bodies, and spontaneously differentiated into at least two different cell types. These cells also reportedly expressed mRNA for the transcription factors OCT4, OCT6 and HES1, a pattern of homeobox genes which is believed to be expressed by ES cells exclusively.

Also recently, Campbell et al., *Nature*, 380:64-68 (1996) reported the production of live lambs following nuclear transfer of cultured embryonic disc (ED) cells from day nine ovine embryos cultured under conditions which promote the isolation of ES cell lines in the mouse. The authors concluded that ED cells from day nine ovine embryos are totipotent by nuclear transfer and that totipotency is maintained in culture.

Van Stekelenburg-Hamers et al., *Mol. Reprod. Dev.*, 40:444-454 (1995), reported the isolation and characterization of purportedly permanent cell lines from inner cell mass cells of bovine blastocysts. The authors isolated and cultured inner cell masses from 8 or 9 day bovine blastocysts under different conditions to determine which feeder cells and culture media are most efficient in supporting the attachment and outgrowth of bovine inner cell mass cells. They concluded that the attachment and outgrowth of cultured inner cell mass cells is enhanced by the use of STO (mouse fibroblast) feeder cells (instead of bovine uterus epithelial cells) and by the use of charcoal-stripped serum (rather than normal serum) to supplement the culture medium. Van Stekelenburg et al reported, however, that their cell lines resembled epithelial cells more than pluripotent inner cell mass cells.

Smith et al., WO 94/24274, published Oct. 27, 1994, Evans et al, WO 90/03432, published Apr. 5, 1990, and Wheeler et al, WO 94/26889, published Nov. 24, 1994, report the isolation, selection and propagation of animal stem cells which purportedly may be used to obtain transgenic animals. Evans et al. also reported the derivation of purportedly pluripotent embryonic stem cells from porcine and bovine species which assertedly are useful for the production of transgenic animals. Further, Wheeler et al, WO 94/26884, published Nov. 24, 1994, disclosed embryonic stem cells which are assertedly useful for the manufacture of chimeric and transgenic ungulates.

Thus, based on the foregoing, it is evident that many groups have attempted to produce ES cell lines, e.g., because of their potential application in the production of cloned or transgenic embryos and in nuclear transplantation.

The use of ungulate inner cell mass (ICM) cells for nuclear transplantation has also been reported. For example, Collas et al., *Mol. Reprod. Dev.*, 38:264-267 (1994) discloses nuclear transplantation of bovine ICMs by microinjection of the lysed donor cells into enucleated mature oocytes. Collas et al. disclosed culturing of embryos in vitro for seven days to produce fifteen blastocysts which, upon transferral into bovine recipients, resulted in four pregnancies and two births. Also, Keefer et al., *Biol. Reprod.*, 50:935-939 (1994), disclosed the use of bovine ICM cells as donor nuclei in nuclear transfer procedures, to produce blastocysts which, upon transplantation into bovine recipients, resulted in several live offspring. Further, Sims et al., *Proc. Natl. Acad. Sci, USA*, 90:6143-6147 (1993), disclosed the production of calves by transfer of nuclei from short-term in vitro cultured bovine ICM cells into enucleated mature oocytes.

The production of live lambs following nuclear transfer of cultured embryonic disc cells has also been reported (Campbell et al., *Nature*, 380:64-68 (1996)). Still further, the use of bovine pluripotent embryonic cells in nuclear transfer and the production of chimeric fetuses has been reported (Stice et al., *Biol. Reprod.*, 54:100-110 (1996); Collas et al, *Mol. Reprod. Dev.*, 38:264-267 (1994)). Collas et al. demonstrated that granulosa cells (adult cells) could be used in a bovine cloning procedure to produce embryos. However, there was no demonstration of development past early embryonic stages (blastocyst stage). Also, granulosa cells are not easily cultured and are only obtainable from females. Collas et al. did not attempt to propagate the granulosa cells in culture or try to genetically modify those cells.

Thomson, U.S. Pat. No. 5,843,780, issued Dec. 1, 1998, reports the purification of primate embryonic stem cells. These cells are reported to be negative for the cell surface marker SSEA-1, positive for the cell surface markers SSEA-3, SSEA-4, TRA-1-60, TRA-1-81 and alkaline phosphatase, and to differentiate into all tissues derived from all three embryonic germ layers (endoderm, mesoderm and ectoderm). Pluripotent embryonic stem cell lines derived from human blastocysts are described by Thomson et al, *Science*, 282:1145-1147 (1998).

In addition, Stice et al, U.S. Pat. No. 5,905,042, issued May 18, 1999, describes cultured inner cell mass cells, and cell lines, derived from ungulates. These cultured inner cell mass cells possess similar morphology and express cell markers identically or substantially similarly to inner cell masses of undifferentiated developing embryos for prolonged culturing periods.

A potential application of embryonic stem cells is to use those cells as a source to produce differentiated cells for cell therapy and for the generation of tissues and organs for transplantation. However, stable embryonic stem cell lines and reliable methods for expansion of those cells into differentiated cells/tissues/organs are not yet available. Therefore, notwithstanding what has previously been reported in the literature, there exists a need for improved sources of cells for cell therapy and for the generation of tissues and organs for transplantation.

OBJECTS AND SUMMARY OF THE INVENTION

It is an object of the invention to provide novel and improved methods for producing mammalian cells which can be used as sources of cells for cell therapy and for the generation of tissues and organs for transplantation.

It is a more specific object of the invention to provide a novel method for inducing inner cell mass cells to differentiate into progenitor cells which can be used for cell therapy or for the generation of tissues and organs for transplantation.

It is an object of the invention to provide an improved method for producing genetically engineered mammalian progenitor cells which can be used as sources of cells for cell therapy and for the generation of tissues and organs for transplantation.

It is a more specific object of the invention to provide a method for inducing genetically engineered inner cell mass cells to differentiate into progenitor cells which can be used for cell therapy or for the generation of tissues and organs for transplantation, wherein a desired gene is inserted, removed or modified in the genetically engineered inner cell mass cells.

It is an object of the invention to provide a method by which progenitor cells derived from an inner cell mass are genetically engineered, and the genetically engineered cells are used as a source of cells for cell therapy and for the generation of tissues and organs for transplantation.

It is another object of the invention to provide a novel method for producing differentiated progenitor cells which involves using a differentiated cell as a nuclear donor for forming a nuclear transfer (NT) unit, producing a morula or blastocyst from the nuclear transfer unit, and inducing cells of the morula or inner cell mass cells from the blastocyst to differentiate into progenitor cells which may be used as a source of cells for cell therapy and for the generation of tissues and organs for transplantation.

It is another object of the invention to provide differentiated progenitor cells produced by using a differentiated cell as a nuclear donor to form a nuclear transfer unit, producing a morula or blastocyst from the nuclear transfer unit, and inducing cells of the morula or inner cell mass cells from the blastocyst to differentiate into progenitor cells.

It is another object of the invention to provide human differentiated progenitor cells produced by using a differentiated human cell as a nuclear donor to form a nuclear transfer unit, producing a morula or blastocyst from the nuclear transfer unit, and inducing cells of the morula or inner cell mass cells from the blastocyst to differentiate into progenitor cells.

Another object of the invention is to culture cells of a morula or inner cell mass cells such that the growth of embryonic stem cells is prevented while the growth of differentiated progenitor cells is promoted.

It is another object of the invention to use such differentiated progenitor cells for therapy or diagnosis.

It is a specific object of the invention to use such differentiated progenitor cells, including human and ungulate differentiated progenitor cells, for treatment or diagnosis of any disease wherein cell, tissue or organ transplantation is therapeutically or diagnostically beneficial. The differentiated progenitor cells may be used within the same species or across species.

It is another object of the invention to use cells derived from NT embryos, including human and ungulate cells, for treatment or diagnosis of any disease wherein cell, tissue or organ transplantation is therapeutically or diagnostically beneficial. The tissues may be used within the same species or across species.

It is another specific object of the invention to use the differentiated cells produced according to the invention in vitro, e.g. for study of cell differentiation and for assay purposes, e.g. for drug studies.

It is another object of the invention to provide improved methods of transplantation therapy, comprising the usage of isogenic or syngenic cells, tissues or organs produced from the differentiated cells produced according to the invention. Such therapies include by way of example treatment of diseases and injuries including Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases.

It is another object of the invention to use the transgenic or genetically engineered differentiated cells produced according to the invention for gene therapy, in particular for the treatment and/or prevention of the diseases and injuries identified, supra.

It is another object of the invention to use the differentiated cells produced according to the invention or transgenic or genetically engineered differentiated cells produced according to the invention as nuclear donors for nuclear transplantation.

Thus, in one aspect, the present invention provides a method for producing differentiated progenitor cells, comprising:

(I) obtaining cells of a morula or inner cell mass cells from a blastocyst; and (ii) inducing differentiation of cells of the morula or inner cell mass cells to produce differentiated progenitor cells.

The differentiated progenitor cells can used to derive cells, tissues and/or organs which are advantageously used in the area of cell, tissue and/or organ transplantation.

In another aspect the present invention provides a method of producing a genetically altered differentiated progenitor cell, by which a desired gene is inserted, removed or modified in the cell used to generate a nuclear transfer unit for use to produce morula for obtaining morula cells or a blastocyst for obtaining inner cell mass cells.

In yet another aspect, the present invention provides a method of producing a lineage-defective human embryonic stem cell, comprising:

I) genetically modifying a human somatic cell such that said somatic cell is incapable of differentiating into a predetermined cell lineage;

ii) generating a nuclear transfer unit using the genetically modified human somatic cell or cell nucleus as the nuclear donor;

iii) activating the resultant nuclear transfer unit;

iv) culturing said activated nuclear transfer unit until greater than the 2-cell developmental stage; and v) culturing cells obtained from said cultured nuclear transfer unit under conditions suitable for the formation of a lineage-defective human embryonic stem cell, said stem cell being unable to differentiate into specific differentiated lineages, such as at least one of the embryonic germ layers.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE PREFERRED EMBODIMENTS

The present invention provides improved procedures for making differentiated progenitor cells for use, for example, in cell therapy or as a source of cells to provide tissues and organs for transplantation. More particularly, morula-derived cells or inner cell mass cells derived from blastocysts are induced to differentiate to differentiated progenitor cells and those differentiated cells are used in cell therapy or as a source of cells to provide tissues and organs for transplantation.

In the past, long-term culture of inner cell mass cells was used to produce embryonic stem cells. Subsequently, the embryonic stem cells were cultured and genetically modified, and induced to differentiate in order to produce cells to make transgenic animals or cells for therapy. By the present invention, the production of embryonic stem cells is bypassed, i.e., morula-derived cells or inner cell mass cells are induced to differentiate directly into differentiated progenitor cells which are then used for cell therapy and for the generation of tissues and organs for transplantation. If desired, genetic modifications can be introduced, for example, into somatic cells prior to nuclear transfer to produce a morula or blastocyst. Thus, the differentiated progenitor cells of the present invention are not pluripotent and are, in essence, tissue-specific stem cells. The differentiated progenitor cells may give rise to cells from all three embryonic germ layers, i.e., endoderm, mesoderm and ectoderm. For example, the differentiated progenitor cells may differentiate into bone, cartilage, smooth muscle, striated muscle and hematopoietic cells (mesoderm); liver, primitive gut and respiratory epithelium (endoderm); or neurons, glial cells, hair follicles and tooth buds (ectoderm).

Furthermore, it is not necessary for the differentiated progenitor cells of the present invention to be immortal, or that the progenitor cells express cell surface markers found on embryonic stem cells, such as the cell surface markers characteristic of primate embryonic stem cells: positive for SSEA-3, SSEA-4, TRA-1-60, TRA-1-81, alkaline phosphatase activity, and negative for SSEA-1. Moreover, the differentiated progenitor cells of the present invention are distinct from embryoid bodies, i.e., embryoid bodies are derived from embryonic stem cells whereas the differentiated stems cells of the present invention are derived from morula-derived cells or from inner cell mass cells.

Preferably, the differentiated progenitor cells of the present invention are produced by culturing morula-derived cells or inner cell mass cells in the absence in the culture of undifferentiated embryonic stem cells. Growth of undifferentiated embryonic stem cells can be prevented, for example, by culturing morula-derived cells or inner cell mass cells in the presence of differentiation-inducing agents or by introducing genetic modifications into the cells such that the growth of embryonic stem cells is prevented.

Any blastocyst may be used as the source of the inner cell mass, including in vitro-fertilization produced blastocysts and blastocysts derived from nuclear transfer units. For methods of producing blastocysts via nuclear transfer units, see U.S. Pat. No. 5,945,577 to Stice et al, the contents of which are hereby incorporated by reference.

Blastocysts may be from any mammalian species, including humans. When blastocysts are derived from nuclear transfer units, the nuclear transfer unit may be the result "same species" transfer, e.g., transfer of a nucleus from a human differentiated cell into a human enucleated oocyte, or "cross species transfer, e.g., transfer of a nucleus from a human differentiated cell into a bovine enucleated oocyte. For production of nuclear transfer units by cross species transfer, see, for example, WO 98/07841, the contents of which are hereby incorporated by reference.

Nuclei from either differentiated or embryonic cells may be used to produce nuclear transfer units. Differentiated mammalian cells are those cells which are past the early embryonic stage. More particularly, differentiated cells are those from at least past the embryonic disc stage (day 10 of bovine embryogenesis).

Methods for isolating inner cell mass cells from blastocysts are known to those of skill in the art. See, for example, U.S. Pat. No. 5,905,042 to Stice et al, and U.S. Pat. No. 5,843,780 to Thomson, the contents both of which are hereby incorporated by reference. Inner cell mass cells from early blastocyte development can be used, or partially differentiated inner cell mass cells from later in blastocyst development can be used according to the present invention.

Isolated inner cell mass cells are induced to differentiate in the absence or presence of cytokines, growth factors, extracellular matrix components, and other factors by any appropriate method. For example, inner cell mass cells can be induced to differentiate in a flat adhesive environment (liquid) or in a 3D adhesive environment (e.g., 1% collagen gel). A microgravity environment can also be used to induce inner cell mass cell differentiation, Ingram et al, *In Vitro Cell Dev Biol Anim*, 33(6):459-466 (1997). Another method of inducing inner cell mass cell differentiation is by generation of teratomas in immunodeficient mice, Thomson et al, *Science*, 282(5391):1145-1147 (1998), or other animals. Differentiation may also be induced by encapsulating the inner cell mass cells and allowing them to form teratomas in an appropriate host. For example, human inner cell mass cells may be encapsulated and place in the same patient from which the inner cell mass cells were derived (isogenic) or a different human (allogeneic). There are currently a number of systems available that allow separation of cells from the immune system of the body by a synthetic, selectively permeable membrane. The membrane allows free exchange of nutrients, oxygen and biotherapeutic substance between blood or plasma and the encapsulated cells. These systems may also modulate the bidirectional diffusion of antigens, cytokines and other immunological moieties based on the chemical characteristics of the membrane and matrix support, Lanza et al, *Nat Biotechnol*, 14(9):1107-1111 (1996). For systems involving implantation of inner cell masses in animals or humans, individual as well as multiple inner cell masses may be implanted in a single animal or human.

Preferably, a screening test is used to detect agents that induce the differentiation of morula-derived cells or inner cell mass cells into desired differentiated cell types. A library of various combinations of differentiation agents is generated. The library of differentiation agents includes, for example, growth factors, cytokines, extracellular matrix components, hormones and hormone antagonists, and neutralizing antibodies to the foregoing. The library of differentiation agents is then tested for the ability to induce differentiation of morula-derived cells or inner cell mass cells. Any of the methods discussed above for inducing differentiation of cells can be used. For example, the cells can be cultured in tissue culture wells, with each well containing a unique combination of differentiation factors. Nucleic acids or cDNAs encoding such factors can also be plated out as naked DNA, or constructs are prepared to carry such nucleic acids by transfection or by viruses. Differentiated cells are identified by use of differentiation-specific antibodies, morphology, PCR using differentiation-specific primers, or any other applicable technique for identifying specific types of differentiated cells.

Differentiation agents which can be used according to the present invention include cytokines such as interferon-alpha A, interferon-alpha A/D, interferon-β, interferon-gamma, interferon-gamma-inducible protein-10, interleukin-1, interleukin-2, interleukin-3, interleukin-4, interleukin-5, interleukin-6, interleukin-7, interleukin-8, interleukin-9, interleukin-10, interleukin-11, interleukin-12, interleukin-13, interleukin-15, interleukin-17, keratinocyte growth factor, leptin, leukemia inhibitory factor, macrophage colony-stimulating factor, and macrophage inflammatory protein-1alpha.

Differentiation agents according to the invention also include growth factors such as 6Ckine (recombinant), activin A, AlphaA-interferon, alpha-interferon, amphiregulin, angiogenin, B-endothelial cell growth factor, beta cellulin, B-interferon, brain derived neurotrophic factor, C10 (recombinant), cardiotrophin-1, ciliary neurotrophic factor, cytokine-induced neutrophil chemoattractant-1, endothelial cell growth supplement, eotaxin, epidermal growth factor, epithelial neutrophil activating peptide-78, erythropoiten, estrogen receptor-alpha, estrogen receptor-B, fibroblast growth factor (acidic/basic, heparin stabilized, recombinant), FLT-3/FLK-2 ligand (FLT-3 ligand), gamma-interferon, glial cell line-derived neurotrophic factor, Gly-His-Lys, granulocyte colony-stimulating factor, granulocyte macrophage colony-stimulating factor, GRO-alpha/MGSA, GRO-B, GRO-gamma, HCC-1, heparin-binding epidermal growth factor like growth factor, hepatocyte growth factor, heregulin-alpha (EGF domain), insulin growth factor binding protein-1, insulin-like growth factor binding protein-1/IGF-1 complex, insulin-like growth factor, insulin-like growth factor II, 2.5 S nerve growth factor (NGF), 7S-NGF, macrophage inflammatory protein-1B, macrophage inflammatory protein-2, macrophage inflammatory protein-3 alpha, macrophage inflammatory protein-3B, monocyte chemotactic protein-1, monocyte chemotactic protein-2, monocyte chemotactic protein-3, neurotrophin-3, neurotrophin4, NGF-B (human or rat recombinant), oncostatin M (human or mouse recombinant), pituitary extract, placenta growth factor, platelet-derived endothelial cell growth factor, platelet-derived growth factor, pleiotrophin, rantes, stem cell factor, stromal cell-derived factor 1B/pre-B cell growth stimulating factor, thrombopoetin, transforming growth factor alpha, transforming growth factor-B1, transforming growth factor-B2, transforming growth factor-B3, transforming growth factor-B5, tumor necrosis factor (alpha and B), and vascular endothelial growth factor.

Differentiation agents according to the invention also include hormones and hormone antagonists, such as 17B-estradiol, adrenocorticotropic hormone, adrenomedullin, alpha-melanocyte stimulating hormone, chorionic gonadotropin, corticosteroid-binding globulin, corticosterone, dexamethasone, estriol, follicle stimulating hormone, gastrin 1, glucagon, gonadotropin, hydrocortisone, insulin, insulin-like growth factor binding protein, L-3,3',5'-triiodothyronine, L-3,3',5-triiodothyronine, leptin, leutinizing hormone, L-thyroxine, melatonin, MZ-4, oxytocin, parathyroid hormone, PEC-60, pituitary growth hormone, progesterone, prolactin, secretin, sex hormone binding globulin, thyroid stimulating hormone, thyrotropin releasing factor, thyroxine-binding globulin, and vasopressin.

In addition, differentiation agents according to the invention include extracellular matrix components such as fibronectin, proteolytic fragments of fibronectin, laminin, thrombospondin, aggrecan, and syndezan.

Differentiation agents according to the invention also include antibodies to various factors, such as anti-low density lipoprotein receptor antibody, anti-progesterone receptor, internal antibody, anti-alpha interferon receptor chain 2 antibody, anti-c-c chemokine receptor 1 antibody, anti-CD 118 antibody, anti-CD 119 antibody, anti-colony stimulating factor-1 antibody, anti-CSF-1 receptor/c-fms antibody, anti-epidermal growth factor (AB-3) antibody, anti-epidermal growth factor receptor antibody, anti-epidermal growth factor receptor, phospho-specific antibody, anti-epidermal growth factor (AB-1) antibody, anti-erythropoietin receptor antibody, anti-estrogen receptor antibody, anti-estrogen receptor, C-terminal antibody, anti-estrogen receptor-B antibody, anti-fibroblast growth factor receptor antibody, anti-fibroblast growth factor, basic antibody, anti-gamma-interferon receptor chain1 antibody, anti-gamma-interferon human recombinant antibody, anti-GFR alpha-1 C-terminal antibody, anti-GFR alpha-2 C-terminal antibody, anti-granulocyte colony-stimulating factor (AB-1) antibody, anti-granulocyte colony-stimulating factor receptor antibody, anti-insulin receptor antibody, anti-insulin-like growth factor-1 receptor antibody, anti-interleukin-6 human recombinant antibody, anti-interleukin-1 human recombinant antibody, anti-interleukin-2 human recombinant antibody, anti-leptin mouse recombinant antibody, anti-nerve growth-factor receptor antibody, anti-p60, chicken antibody, anti-parathyroid hormone-like protein antibody, anti-platelet-derived growth factor receptor antibody, anti-platelet-derived growth factor receptor-B antibody, anti-platelet-derived growth factor-alpha antibody, anti-progresterone receptor antibody, anti-retinoic acid receptor-alpha antibody, anti-thyroid hormone nuclear receptor antibody, anti-thyroid hormone nuclear receptor-alpha 1/Bi antibody, anti-transferrin receptor/CD71 antibody, anti-transforming growth factor-alpha antibody, anti-transforming growth factor-B3 antibody, anti-tumor necrosis factor-alpha antibody, and anti-vascular endothelial growth factor antibody.

Once subjected to the differentiation protocol, primitive cells from a particular embryonic lineage can be isolated from the differentiated inner cell mass derivatives by conventional techniques. If desired, the isolated differentiated progenitor cells can be expanded, for example, by cell culture or other appropriate methods. By the present invention, the differentiated progenitor cells are obtained through differentiated inner cell mass cells without having to generate embryonic stem cells.

The differentiated progenitor cells can also be transfected. Transfection can be performed during any appropriate stage during the production of the differentiated progenitor cells. For example, before blastocyst formation, differentiated cells used as nuclear donors for formation of nuclear transfer units can be transfected. Another possibility is to transfect the differentiated progenitor cells after they have been isolated, e.g., transfection of CD34+, CD38– cells of the hematopoietic system.

Any known method for inserting, deleting or modifying a desired gene from a mammalian cell may be used for producing the transfected differentiated progenitor cells. These procedures may remove all or part of a gene, and the gene may be heterologous. Included is the technique of homologous recombination, which allows the insertion, deletion or modification of a gene or genes at a specific site or sites in the cell genome.

A retroviral high-throughput screening procedure can also be used to identify genes involved in lineage determination in embryonic stem cells. Those lineage-determinant genes can then be inserted and/or induced in morula-derived cells or inner cell mass cells used to produce differentiated progenitor cells. An example of retroviral-mediated screening is as follows.

A. Construction of Retroviral Library

A retroviral cDNA library is constructed from a differentiated tissue (e.g., neurons, heart muscle cells, hematopoietic stem cells (CD34+) cells or other differential cells). These libraries can be built using any Moloney-based vector system. Commercially available examples are pBabe and pLIB vectors (Clontech). Already constructed libraries from muscle, liver and brain can also be obtained from commercial sources (Clontech). Furthermore, construction of specialized libraries can be simply achieved.

B. Development of the Functional Screen in ES Cells

Primate or mammalian ES cells are transfected with a reporter gene construct which is composed of the promoter of a tissue specific gene, for example, a CD34 promoter linked to GFP protein. This promoter reporter construct is then transfected into ES cells. Clones are selected that have minimum background activity and a positive control cell line (KG-1) would be used to ensure expression of the promoter construct.

C. Packaging of the Retroviral Library

The retroviral cDNA library is subsequently efficiently transfected (>80% frequency) into 293 based EcoPack or AmphoPack cell lines (Clontech). These cell lines express the Gag-pol and Envelope proteins required for efficient packaging. The high ($>10^6$) titre production of virus in these cell lines makes them ideal for library representation. In case of problems associated with these lines, an alternative system can be constructed by stable transfection of Gag-pol and Env genes into 293 cells.

D. The Screen

The ES-Rep (reporter) cells are subsequently infected with the packaged retroviruses at the multiplicity of infection of 1 (MOI=1). Upon infection, the ES-Rep cells are allowed to recover and divide. These cells are then subjected to Fluorescent Activated Cell Sorting (FACs) and the GFP+ cells are selected, re-cultured and allowed to recover. Genomic DNA is prepared from these cells and subjected to PCR amplification using primers which amplify the retroviral cDNA insert. These inserts are then individually sequenced and tested for their ability to upregulate GFP in ES-Rep cells. Alternatively the cDNAs can be recovered as a pool and then be infected into virgin ES-Rep cells to enrich for the event of interest (GFP+). The individual cDNA clones are then further characterized for their ability to elicit the desired phenotype, i.e., their ability to turn ES cells into neuronal, muscle or other desired lineages. See Deiss, L. P. et al., 1995, Genes Dev. 9:15; Whitehead, I. et al, 1995, MCB 15:704; Rayner, J. R. et al, 1994, Ibid. 14:880; Goldfarb, M. et al, 1982, Nature 296: 4.04; Gudkov, A. V. et al, 1993, PNAS 90:3231; and Deiss, L. P. & Kimchi, A., 1991, Science, 252:117; the contents all of which are hereby incorporated by reference.

Transplanted embryonic stem cells are known to be capable of not only forming benign teratomas, but malignant tumors as well. To eliminate the risk of both benign and malignant tumors in the process of the present invention, it is useful to introduce or delete genes from cells (e.g., cells used as nuclear donors for nuclear transfer) that prevent the growth of undifferentiated embryonic cells in culture. For example, an inducible promoter such as the MMTV promoter can be introduced into cells, followed by induction with dexamethasone to drive the expression of a gene that blocks the growth of undifferentiated cells, or induces their differentiation. Another possibility is to introduce a promoter for a gene that is germ line-specific to drive the expression of a cell cycle blocker or an apoptosis gene. Alternatively, undifferentiated embryonic stem cells can be identified and eliminated.

A preferred method of making differentiated progenitor cells comprises obtaining a human embryo by in vitro fertilization or by nuclear transfer, and culturing the embryo until the blastocyst stage in G1.2/G2.2 culture media. Zona pellucida is removed from the embryo using mild digestion with pronase. Trophoblastic cells are removed from the embryo by immunosurgery. Inner cell mass cells are induced to differentiate with or without cytokines by any of: a) flat adhesive environment; b) 3D adhesive environment; c) microgravity;

d) generation of teratomas in immunodeficient mice; or e) formation of teratomas from encapsulated inner cell mass cells in isogenic or allogenic humans. Differentiated progenitor cells of a particular embryonic lineage are then isolated from the differentiated inner cell mass derivatives.

The resultant differentiated progenitor cells of the present invention, preferably human differentiated progenitor cells, have numerous therapeutic and diagnostic applications. Most especially, such differentiated progenitor cells may be used for cell transplantation therapies. Human differentiated progenitor cells have application in the treatment of numerous disease conditions.

The subject differentiated progenitor cells may be used to obtain any desired differentiated cell type. Therapeutic usages of such differentiated human cells are unparalleled. For example, human hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, obtaining inner cell mass cells as described above, and culturing such cells under conditions which favor differentiation, until hematopoietic stem cells are obtained. Such hematopoietic cells may be used in the treatment of diseases including cancer and AIDS.

Alternatively, adult somatic cells from a patient with a neurological disorder may be fused with an enucleated oocyte, human inner cell mass cells obtained therefrom, and such cells cultured under differentiation conditions to produce neural cell lines. Specific diseases treatable by transplantation of such human neural cells include, by way of example, Parkinson's disease, Alzheimer's disease, ALS and cerebral palsy, among others. In the specific case of Parkinson's disease, it has been demonstrated that transplanted fetal brain neural cells make the proper connections with surrounding cells and produce dopamine. This can result in long-term reversal of Parkinson's disease symptoms.

The great advantage of the subject invention is that it provides an essentially limitless supply of isogenic or syngenic human cells suitable for transplantation. Therefore, it will obviate the significant problem associated with current transplantation methods, i.e., rejection of the transplanted tissue which may occur because of host-vs-graft or graft-vs-host rejection. Conventionally, rejection is prevented or reduced by the administration of anti-rejection drugs such as cyclosporine. However, such drugs have significant adverse side-effects, e.g., immunosuppression, carcinogenic properties, as well as being very expensive. The present invention should eliminate, or at least greatly reduce, the need for anti-rejection drugs.

Other diseases and conditions treatable by isogenic cell therapy include, by way of example, spinal cord injuries, multiple sclerosis, muscular dystrophy, diabetes, liver diseases, i.e., hypercholesterolemia, heart diseases, cartilage replacement, burns, foot ulcers, gastrointestinal diseases, vascular diseases, kidney disease, urinary tract disease, and aging related diseases and conditions.

This methodology can be used to replace defective genes, e.g., defective immune system genes, cystic fibrosis genes, or to introduce genes which result in the expression of therapeutically beneficial proteins such as growth factors, lymphokines, cytokines, enzymes, etc. For example, the gene encoding brain derived growth factor may be introduced into human inner cell mass cells, the cells differentiated into neural cells and the cells transplanted into a Parkinson's patient to retard the loss of neural cells during such disease.

Previously, cell types transfected with BDNF varied from primary cells to immortalized cell lines, either neural or non-neural (myoblast and fibroblast) derived cells. For example, astrocytes have been transfected with BDNF gene using retroviral vectors, and the cells grafted into a rat model of Parkinson's disease (Yoshimoto et al., *Brain Research,* 691:25-36, (1995))

This ex vivo therapy reduced Parkinson's-like symptoms in the rats up to 45% 32 days after transfer. Also, the tyrosine hydroxylase gene has been placed into astrocytes with similar results (Lundberg et al., *Develop. Neurol.,* 139:39-53 (1996) and references cited therein).

However, such ex vivo systems have problems. In particular, retroviral vectors currently used are down-regulated in vivo and the transgene is only transiently expressed (review by Mulligan, *Science,* 260:926-932 (1993)). Also, such studies used primary cells, astrocytes, which have finite life span and replicate slowly. Such properties adversely affect the rate of transfection and impede selection of stably transfected cells. Moreover, it is almost impossible to propagate a large population of gene targeted primary cells to be used in homologous recombination techniques. By contrast, the difficulties associated with retroviral systems should be eliminated by the use of differentiated progenitor cells.

Genes which may be introduced into the subject differentiated progenitor cells include, by way of example, epidermal growth factor, basic fibroblast growth factor, glial derived neurotrophic growth factor, insulin-like growth factor (I and II), neurotrophin-3, neurotrophin-4/5, ciliary neurotrophic factor, AFT-1, cytokine genes (interleukins, interferons, colony stimulating factors, tumor necrosis factors (alpha and beta), etc.), genes encoding therapeutic enzymes, etc.

In addition to the use of human differentiated progenitor cells in cell, tissue and organ transplantation, the present invention also includes the use of non-human cells in the treatment of human diseases. Thus, differentiated progenitor cells of any species may be used in the treatment of human disease conditions where cell, tissue or organ transplantation is warranted. In general, differentiated progenitor cells according to the present invention can be used within the same species (autologous, syngenic or allografts) or across species (xenografts).

Also, the subject differentiated progenitor cells, preferably human cells, may be used as an in vitro model of differentiation, in particular for the study of genes which are involved in the regulation of early development.

Also, differentiated cell tissues and organs using the subject differentiated progenitor cells may be used in drug studies.

The present invention also provides a method of creating lineage-defective human embryonic stem cells. Such cells are derived from a human pre-embryo produced by nuclear transfer. If the hypothetical case of transferring such an embryo into the uterus of a woman, it would never develop into a human being.

To produce a lineage-defective embryonic stem cell, preferably lineage-defective human embryonic stem cell a somatic cell is genetically engineered to be incapable of differentiation into a particular cell lineage. Such genetic modifications include knockout of selected genes, or expression of appropriate antisense nucleic acids or ribozymes. Examples of knockout genes or genes not allowed to be expressed are serum response factor (SRF) (Arsenian et al, *EMBO J,* 17(2.1):6289-6299, 1998), MESP-1 (Saga, *Mech Dev,* 75(1-2):53-66, 1998), HNF-4 (Chen et al, *Genes Dev,* 8(20):2466-

2477, 1994), beta1 integrin (Rohwedel et al, *Dev Biol,* 201 (2):167-184, 1998) and MSD (Holdener et al, *Development,* 120(5):1335-1346, 1994), for mesoderm; GATA-6 (Morrisey et al, *Genes Dev,* 12(22):3579-3590, 1998) and GATA-4 (Soudais et al, *Development,* 121(11):3877-3888, 1995), for endoderm; and RNA helicase A (Lee et al, *Proc Natl Acad Sci USA,* 95(23):13709-13713, 1998) and H beta 58 (Radice et al, *Development,* 111(3):801-811, 1991), for ectoderm. The invention further embraces the introduction of one or more genetic modifications that prevent differentiation of particular cell lineages, e.g. neural cells. Methods and vectors for effecting gene knockout are subject of numerous patents, including U.S. Pat. Nos. 5,110,735, 6,074,853, 5,998,144, 5,948,653, 5,945,339, 5,925,544, 5,869,718, 5,830,698, 5,780,296, 5,614,396, 5,612,205, 5,468,629, 5,093,257, all of which are incorporated by reference in their entirety herein.

Other genes that my be deleted or inactivated that are involved in specific cell lineages include by way of example ICSBP, hedgehog, Cbfal, VASA, HESXI, transcription factors, among many others. Recently, Sato, et al., *Mol. Reprod. Devel.* 56(1): 34-44 (2000) reported a genetic approach for identifying genes involved in specific cell lineages that uses the Cre-LoxP_system, that is incorporated by references in its entirety herein.

The genetically engineered cells are then used as nuclear donors for generation of nuclear transfer units. Human oocytes or any other mammalian eggs, e.g., bovine, may be used as the recipient of the nuclear donor. The nuclear transfer units are allowed to development to blastocysts as described above, and lineage-defective human embryonic stem cells are derived therefrom. For methods relating to generation of human embryonic stems cells, see for example, Thomson et al, *Science,* 282:1145-1147, 1998 and U.S. Pat. No. 5,843,780. Upon induction of differentiation, the lineage-defective human embryonic stem cells will not differentiate into at least one of the embryonic germ layers (mesoderm, endoderm or ectoderm). If desired, the lineage-defective human embryonic stem cells can also be engineered to be "mortal", for example by expression of an antisense or ribozyme telomerase gene.

While the foregoing aspect of the invention has been described with respect to lineage-defective human embryonic stem cells, the present invention also includes lineage-defective embryonic stem cells for any mammalian species.

In order to more clearly describe the subject invention, the following examples are provided. Such examples are provided by way of illustration and not by way of limitation.

EXAMPLE 1

The following example illustrates that only a fraction of the inner cell mass cells cultured are capable of developing into embryonic stem cell-like cells. Thus, there are pluripotent inner cell mass cells which cannot, or do not, develop into embryonic stem cells.

Explant Derivation and Culture
A. Sample Retrieval
  1) Thoroughly clean the section of tissue to be removed, such as by use of an iodine or ethanol solution.
  2) Remove sample with an ear notcher or scissors and immediately place the tissue in an antibiotic solution (Solution 1 or equivalent). Swirl solution to remove any remaining iodine.
  3) Transfer to a 50 ml conical tube of fresh Solution 1.
  4) Store or ship overnight at 4° C.

B. Tissue Sectioning and Culture
  1) Remove sample from conical tube and place in fresh warm Solution I in a 100 mm culture dish.
  2) Trim any hair using sterile forceps and scissors and transfer to another dish of Solution 1.
  3) Use forceps and a sterile scalpel to carefully cut very thin sections of tissue. Thinner sections will yield more cells.
  4) Place the sections flat on the bottom center of tissue culture dishes and cover with sterile glass slides.
  5) Flood the dishes with ~10 ml normal culture media and place in an incubator at 5% $CO_2$ and 37° C.
  6) Culture explant samples for 10 days, changing media once.
  7) Remove media, rinse with DPBS and add 5 ml trypsin solution (0.08% trypsin and 0.02% EDTA)
  8) Place on a warming plate until cells loosen.
  9) Remove solution from plates and place in a 50 ml conical tube with an equal amount of warm culture media (10% FBS).
  10) Spin down cells.
  11) Remove supernatant and re-suspend cell pellet in normal media.
  12) Culture.

Solution 1

| | |
|---|---|
| DPBS (Biowhittaket, 04-479Y) | 200 ml |
| Ciprofloxacin IICL (Mediatech, 61-277) | 2.33 mg |
| Fungizone (Gibco, 15295-017) | 1.5 ml |

In Vitro Maturation of Bovine Oocytes

Ovaries are recovered at a slaughterhouse, placed in warm PBS (34° C.) and brought to the laboratory within 8 hours. Each follicle of more than 2 mm in diameter is aseptically aspirated with an 18 G needle. Search of oocytes is performed in modified Tyrode's medium (TL Hepes). Oocytes with a homogeneous cytoplasm, considerable perivitelline space and intact cumulus cells are placed in maturation medium M199 (GIBCO), 10% FCS, 5 µl/ml bFSH (Nob1), 5 µl/ml bLH (Nob1) and 10 µl/ml Penstrep (Sigma) for 22 h at 38.5° C. and 5% $CO_2$.

Nuclear Transplantation

Eighteen hours post maturation, oocytes are placed in a 100 µl drop of TL HECM-Hepes under mineral oil (Sigma). Oocyte enucleation (extraction of chromosomes) is performed using a beveled glass pipette of 25 µm diameter. Evaluation of enucleation is done by exposure of individual oocytes previously cultured for 15 min in 1 µg/ml of bisBENZIMIDE (Hoechst 33342, Sigma) in TL HECM-Hepes under UV light. Donor cells are placed in the perivitelline space and fused with the egg's cytoplasm at 23 hours post maturation.

Embryo Culture

During the first 3 days after fertilization, embryos are cultured in 500 µl well plates with mouse embryonic fibroblast (MF) feeder layers in ACM media with 10% fetal calf serum. On day 4, embryos were transferred to 500 µl well plates with mouse fibroblast (MF) feeder layers, and fresh ACM media with 10% FCS until blastocyst stage.

ES-Like Cell Culture

Blastocysts are placed in a 32 mm plate (Nunc) with a mitotically inactivated MF feeder layer and ES medium (DMEM-high glucose, 15% fetal calf serum, 4 µl/ml antibiotic-antimycotic, 2.8 µl/ml 2-mercaptoethanol, 0.3 mg/ml L-glutamine, 10 µl/ml of non-essential amino acids and 1 µl/ml tylosin tartrate) equilibrated a day in advance at 38.5° C. and 5% $CO_2$. Using a 22 G needle, the zona pellucida and trophoblast cells of the blastocyst are mechanically removed. The remaining inner cell mass (ICM) is placed on top of the MF. After one to two weeks in culture, ES-like cells are passaged to a fresh mitotically inactivated MF. Inactivation of MF is performed by exposing them to gamma radiation (2956 rads). ES-like cells are passaged by cutting a small piece (50 to 100 cells) of the colony and placing it on top MF feeder layers using a pulled Pasteur pipette.

By the above procedure, 41 bovine embryos were reconstructed from transgenic adult somatic cells. Of those 41 embryos, 15 (or 37%) generated embryonic stem cell-like cells when inner cell mass cells were cultured under the above conditions. However, 26 of the embryos could not produce embryonic stem cell-like cells in spite of culturing inner cell mass cells under ideal conditions for stem cell generation.

It is unclear if the timing of embryo development, intrinsic differences of individual embryos, or the particular culture conditions (e.g., the presence or absence of various growth factors) might have been responsible for only a fraction of the inner cell masses developing into embryonic stem cell-like cells. Regardless, these results indicate that there are pluripotent inner cell mass cells which cannot, or do not, develop into embryonic stem cells. These inner cell mass cells which do not develop into embryonic stem cells should also be of therapeutic value. It should be noted that Thompson et al (*Science,* 282:1145-1147, 1998) reported the production of human embryonic stem cells in which only S of 14 (or 36%) inner cell mass cells developed into ES cell lines. Thus, the existence of inner cell mass cells which do not develop into embryonic stem cells appears to be a widespread phenomenon among mammalian species.

EXAMPLE 2

Three adult Holstein steers approximately 8-10 months old (weighing approximately 500-1000 lbs) were purchased from Thomas Morris, Inc., Maryland, and shipped to the South Deerfield Farm at the University of Massachusetts, Amherst. To obtain fibroblasts for nuclear transfer, skin biopsies were obtained from each of the animals by ear notch. A plasmid which expresses a reporter gene encoding enhanced green fluorescent protein (eGFP), was transfected into the cells, and transfected cells were selected with neomycin. Purified cells, analyzed by PCR and/or FISH, were used for nuclear transfer as described previously in *Nature* (2998) *Biotechnol.* 16: 642-646, herein incorporated by reference.

Isolated inner cell mass cells generated from bovine blastocysts are then injected into the paralumbar fascia of the donor steers (three sites with inner mass cells from three 10 day embryos, three sites with inner mass cells from three 12 day embryos, and three sites with inner mass cells from three 14 day embryos, per animal). The inner cell masses are derived from the same animal into which they are injected and, thus, the inner cell masses are immune compatible with the steers. After two months, the muscle is examined for teratoma formation. Any tumors identified are removed for histological analysis.

The procedure is performed on the standing animal using 20 mg Xylazine/8 mg Butorphanol Tatrate administered IV in the tail vein. The paralumbar fascia area is clipped and surgically prepared, using 100 ml of 2% Lidocaine as a local anesthetic administered as a paralumbar block. The animals should be given antibiotics for three days post-surgically as a precautionary measure (Ceftlofur Hcl 50 mg/cc @ 1 cc/100 pounds). Immediately following surgery a single injection of Flunixin Meglumine @ 1 cc/100 pounds may be given to control pain and swelling at the surgical site. If teratoma formation does not occur at the paralumbar fascia, other sites may be analyzed, i.e., subcutaneously.

It is expected that cells from all three germ layers, i.e., ectoderm, mesoderm, and endoderm, will be observed in teratomas.

While the invention has been described in detail and with reference to specific embodiments thereof, it will be apparent to one skilled in the art that various changes and modifications can be made therein without departing from the spirit and scope thereof.

What is claimed is:

1. A method of producing differentiated cells, comprising:
   i) obtaining morula cells or inner cell mass cells from a human blastocyst by mechanical and/or enzymatic means; and
   ii) inducing the morula cells or inner cell mass cells to differentiate directly into differentiated cells, wherein the inducing step comprises a) addition of a differentiating agent directly to the morula cells or inner cell mass cells or b) placement of the morula cells or inner cell mass cells directly in a differentiation environment chosen from a flat adhesive environment, a microgravity environment and a 3D adhesive environment; and
   iii) isolating the differentiated cells from ii), thereby producing differentiated cells.

2. The method according to claim 1, wherein said blastocyst is produced by in vitro fertilization.

3. The method according to claim 1, wherein said blastocyst is produced from a nuclear transfer unit.

4. The method according to claim 3, wherein a desired DNA is inserted, removed or modified in said nuclear transfer unit, thereby resulting in the production of a genetically altered differentiated cell.

5. The method according to claim 1, wherein said morula cells or inner cell mass cells are induced to differentiate in a flat adhesive environment.

6. The method according to claim 1, wherein said morula cells or inner cell mass cells are induced to differentiate in a 3D adhesive environment.

7. The method according to claim 1, wherein said morula cells or inner cell mass cells are induced to differentiate in a microgravity.

8. A method of producing differentiated cells, comprising:
   i) obtaining morula cells or inner cell mass cells from a human blastocyst by mechanical and/or enzymatic means; and
   ii) inducing the morula cells or inner cell mass cells to differentiate directly into differentiated cells, wherein the inducing step comprises a) addition of a differentiating agent directly to the morula cells or inner cell mass cells or b) placement of the morula cells or inner cell mass cells directly in a differentiation environment wherein the morula or inner cell mass cells are induced to differentiate by generation of teratomas in immunodeficient mice; and
   iii) isolating the differentiated cells from ii), thereby producing differentiated cells.

9. The method according to claim 1, wherein the differentiated cells are differentiated progenitor cells.

10. The method according to claim 9, wherein the differentiated progenitor cells give rise to mesoderm.

11. The method according to claim 9, wherein the differentiated progenitor cells give rise to ectoderm.

12. The method according to claim 9, wherein the differentiated progenitor cells give rise to endoderm.

13. A method of producing differentiated cells, the method comprising:

i) obtaining morula cells or inner cell mass cells from a human blastocyst by mechanical and/or enzymatic means; and ii) inducing the morula cells or inner cell mass cells to differentiate directly into differentiated cells, wherein the inducing step consists of a) addition of a differentiating agent directly to the morula cells or inner cell mass cells or b) placement of the morula cells or inner cell mass cells directly in a differentiation environment chosen from a flat adhesive environment, a microgravity environment, and a 3D adhesive environment, thereby producing differentiated cells.

14. A method of producing differentiated cells, the method consisting of;

i) obtaining morula cells or inner cell mass cells from a human blastocyst by mechanical and/or enzymatic means; and ii) inducing the morula cells or inner cell mass cells to differentiate directly into differentiated cells, wherein the inducing step consists of a) addition of a differentiating agent directly to the morula cells or inner cell mass cells or b) placement of the morula cells or inner cell mass cells directly in a differentiation environment chosen from a flat adhesive environment, a microgravity environment and a 3D adhesive environment; and iii) isolating the differentiated cells from ii), thereby producing differentiated cells.

15. A method comprising:

i) obtaining morula cells or inner cell mass cells from a human blastocyst by mechanical and/or enzymatic means; and ii) contacting the obtained morula cells or inner cell mass cells with a differentiating agent.

* * * * *